(12) United States Patent
Vargas

(10) Patent No.: US 10,646,380 B2
(45) Date of Patent: May 12, 2020

(54) FEMININE NIGHT PAD

(71) Applicant: Asalia Vargas, Brownwood, TX (US)

(72) Inventor: Asalia Vargas, Brownwood, TX (US)

( * ) Notice: Subject to any disclaimer, the term of this patent is extended or adjusted under 35 U.S.C. 154(b) by 430 days.

(21) Appl. No.: 15/596,908

(22) Filed: May 16, 2017

(65) Prior Publication Data
US 2017/0281420 A1 Oct. 5, 2017

Related U.S. Application Data

(63) Continuation-in-part of application No. 29/560,028, filed on Apr. 1, 2016, now Pat. No. Des. 787,048.

(51) Int. Cl.
A61F 13/472 (2006.01)
A61F 13/475 (2006.01)
A61F 13/51 (2006.01)
A61F 13/53 (2006.01)
A61F 13/47 (2006.01)

(52) U.S. Cl.
CPC .... A61F 13/47254 (2013.01); A61F 13/4756 (2013.01); A61F 2013/4708 (2013.01); A61F 2013/51078 (2013.01); A61F 2013/530029 (2013.01); A61F 2013/53089 (2013.01); A61F 2013/530788 (2013.01); A61F 2013/530868 (2013.01)

(58) Field of Classification Search
CPC .. A61F 2013/530029; A61F 2013/4708; A61F 13/47254; A61F 2013/530547
See application file for complete search history.

(56) References Cited

U.S. PATENT DOCUMENTS 3,115,877 A * 12/1963 Harwood .......... A61F 13/47245
604/375
3,732,867 A * 5/1973 Money ................ A61F 13/8405
604/360
4,657,538 A * 4/1987 Becker .............. A61F 13/53717
604/378
4,950,264 A * 8/1990 Osborn ............. A61F 13/15203
604/385.08

(Continued)

FOREIGN PATENT DOCUMENTS

EP 1222906 A1 * 7/2002 .......... A61F 13/472
WO WO-0072790 A1 * 12/2000 ....... A61F 13/47218
WO WO-0135887 A1 * 5/2001 ....... A61F 13/15203

OTHER PUBLICATIONS

Examiner's Report in related Canadian Intellectual Property Office application 170457, dated Dec. 12, 2016, 2 pages.

Primary Examiner — Susan S Su
(74) Attorney, Agent, or Firm — Law Office of Jeff Williams, PLLC; J. Oliver Williams

(57) ABSTRACT

A feminine night pad is described having multiple layers of absorbent material selectively stacked in a manner to define a body portion and a central portion. Each portion is laid upon an upper surface of a trim member including an impermeable sheet. The body portion has a plurality of absorbing layers set in from the edge of the trim member. The central portion is built upon the body portion and includes one or more layers of additional absorbent material. The trim member is covered in absorbent material and extends around the entire periphery of the body portion. The trim member and corresponding portions are formed into a triangular shape to better conform to a woman's body.

8 Claims, 4 Drawing Sheets

(56) References Cited

U.S. PATENT DOCUMENTS

| | | | | |
|---|---|---|---|---|
| 5,593,398 A * | 1/1997 | Weimer | A61F 13/47254 | 2/406 |
| 5,683,373 A * | 11/1997 | Darby | A61F 13/47254 | 604/385.01 |
| 5,729,835 A * | 3/1998 | Williams | A61F 13/47254 | 2/400 |
| 5,792,129 A * | 8/1998 | Johansson | A61F 13/472 | 604/387 |
| 6,117,523 A * | 9/2000 | Sugahara | A61F 13/51121 | 428/134 |
| 6,610,902 B1 * | 8/2003 | Gustafsson | A61F 13/47227 | 604/367 |
| 6,620,144 B1 * | 9/2003 | Glasgow | A61F 13/47227 | 604/385.01 |
| 6,814,721 B1 * | 11/2004 | Hansson | A61F 13/47254 | 604/374 |
| 6,908,456 B1 * | 6/2005 | Drevik | A61F 13/47254 | 604/385.01 |
| 7,291,136 B1 * | 11/2007 | Drevik | A61F 13/47254 | 604/385.01 |
| 2001/0053900 A1 * | 12/2001 | Drevik | A61F 13/47254 | 604/378 |
| 2002/0010451 A1 * | 1/2002 | Helmfridsson | A61F 13/15699 | 604/385.05 |
| 2002/0115978 A1 * | 8/2002 | Cole | A61F 13/47254 | 604/385.101 |
| 2002/0120247 A1 * | 8/2002 | Mizutani | A61F 13/47218 | 604/385.17 |
| 2003/0097109 A1 * | 5/2003 | Bruce | A61F 13/47236 | 604/385.01 |
| 2003/0153890 A1 * | 8/2003 | Rosenfeld | A61F 13/15203 | 604/385.04 |
| 2004/0102747 A1 * | 5/2004 | Bell | A41B 9/002 | 604/358 |
| 2006/0264885 A1 * | 11/2006 | Carstens | A61F 13/47254 | 604/396 |
| 2006/0276766 A1 * | 12/2006 | Kentolall | A61F 13/47254 | 604/385.01 |
| 2008/0249494 A1 * | 10/2008 | Digiacomantonio | A61F 13/5611 | 604/378 |
| 2012/0253304 A1 * | 10/2012 | Scott | A61F 13/15699 | 604/365 |
| 2013/0296820 A1 * | 11/2013 | Hughes | A61F 13/47254 | 604/385.01 |
| 2016/0302978 A1 * | 10/2016 | Lindstrom | A61F 13/4704 | |
| 2017/0239102 A1 * | 8/2017 | Lee | A61F 13/5611 | |

* cited by examiner

FEMININE NIGHT PAD

CLAIM OF PRIORITY

This application claims the benefit of and is a Continuation In Part application of U.S. Design Application No. 29/560,028, filed 1 Apr. 2016. The information contained therein is hereby incorporated by reference.

BACKGROUND

1. Field of the Invention

The present application relates to a detachable undergarment lining, and more particularly to a feminine sanitary pad used to prevent leakage during menstruation.

2. Description of Related Art

Women experience menstruation typically every 28 days. At this time their bodies discharge an amount of bodily fluid through the vaginal canal. The amount of fluid can change depending on the woman and some environmental factors. Typically women use either a tampon or a sanitary napkin (pad) to absorb this discharged fluid and contain it. Both tampons and sanitary napkins utilize absorbable materials to accomplish this.

With respect to sanitary napkins, they frequently are a liner that is coupled to an inside portion of an undergarment. Conventional sanitary napkins comprise at least one layer of absorbent material, one side of which is directed toward the body and the other side, customarily with an adhesive strip, is placed against the undergarment. These are shaped usually in a general rectangular form. The anatomical variation of the female human body is great. Conventional napkins are designed for the average; therefore, they may not always fit every user comfortably. During daily activities, these work fairly well. However, at night when the woman is lying down and moving between positions, conventional napkins can become unaligned or dislodged from their position, leading to leakage.

Although strides have been made with respect to sanitary napkins for women, considerable shortcomings remain.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

Figure 1:
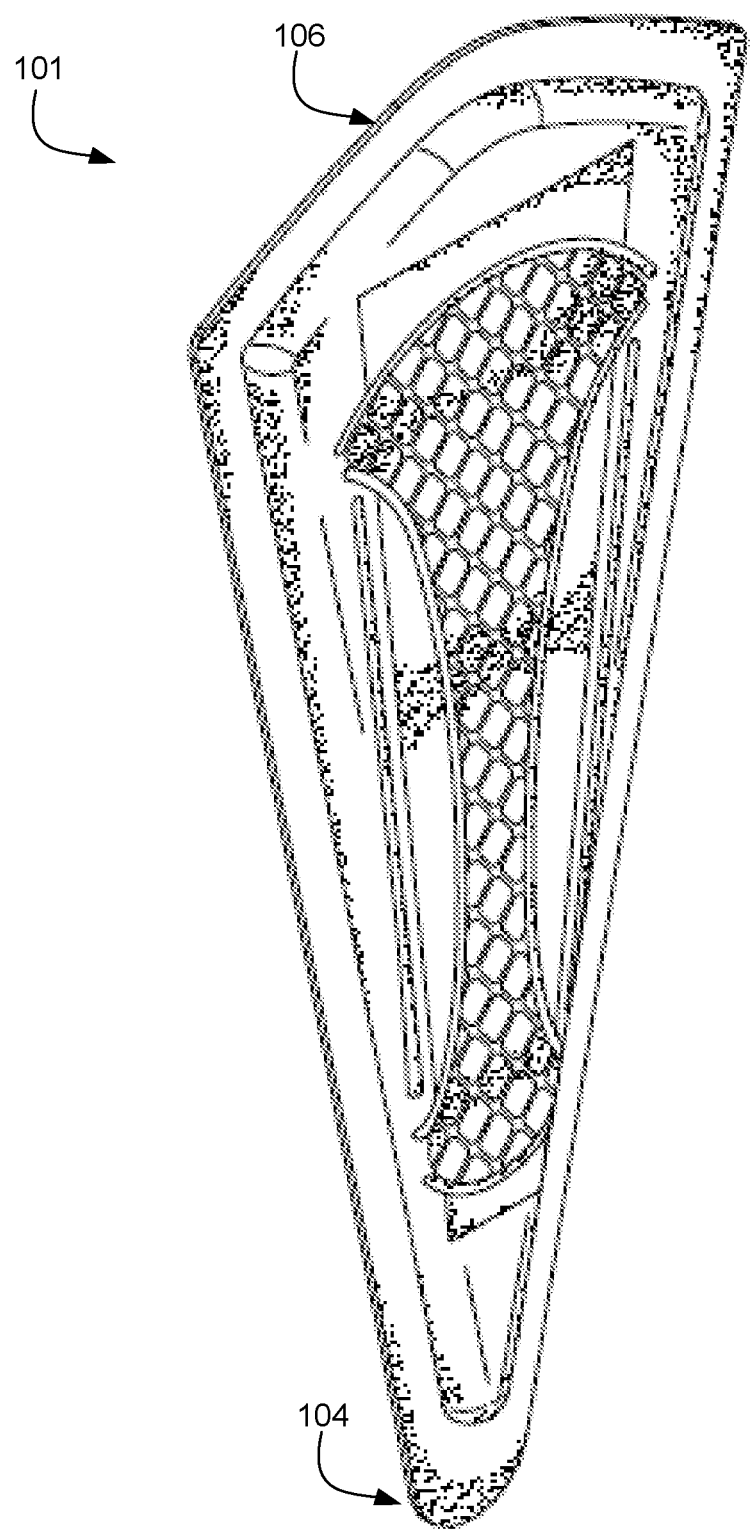
FIG. 1 is a perspective view of a feminine night pad according to an embodiment of the present application.

While the pad of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The pad and method in accordance with the present application overcomes one or more of the above-discussed problems commonly associated with traditional sanitary napkins. In particular, the feminine night pad is configured to include a plurality of absorbing layers that surround a singular gel layer. The feminine night pad is configured to have a relative triangular shape to more accurately fit the contour of a woman. Additionally, the feminine night pad includes a plurality of textured ribbing to direct flow in an effort to mitigate potential leakage. These and other unique features of the device are discussed below and illustrated in the accompanying drawings.

The device and method will be understood, both as to its structure and operation, from the accompanying drawings, taken in conjunction with the accompanying description. Several embodiments of the device may be presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

Referring now to the drawings wherein like reference characters identify corresponding or similar elements in form and function throughout the several views. FIGS. 1-4 illustrate assorted views of feminine night pad 101. In FIG.

Figure 2:
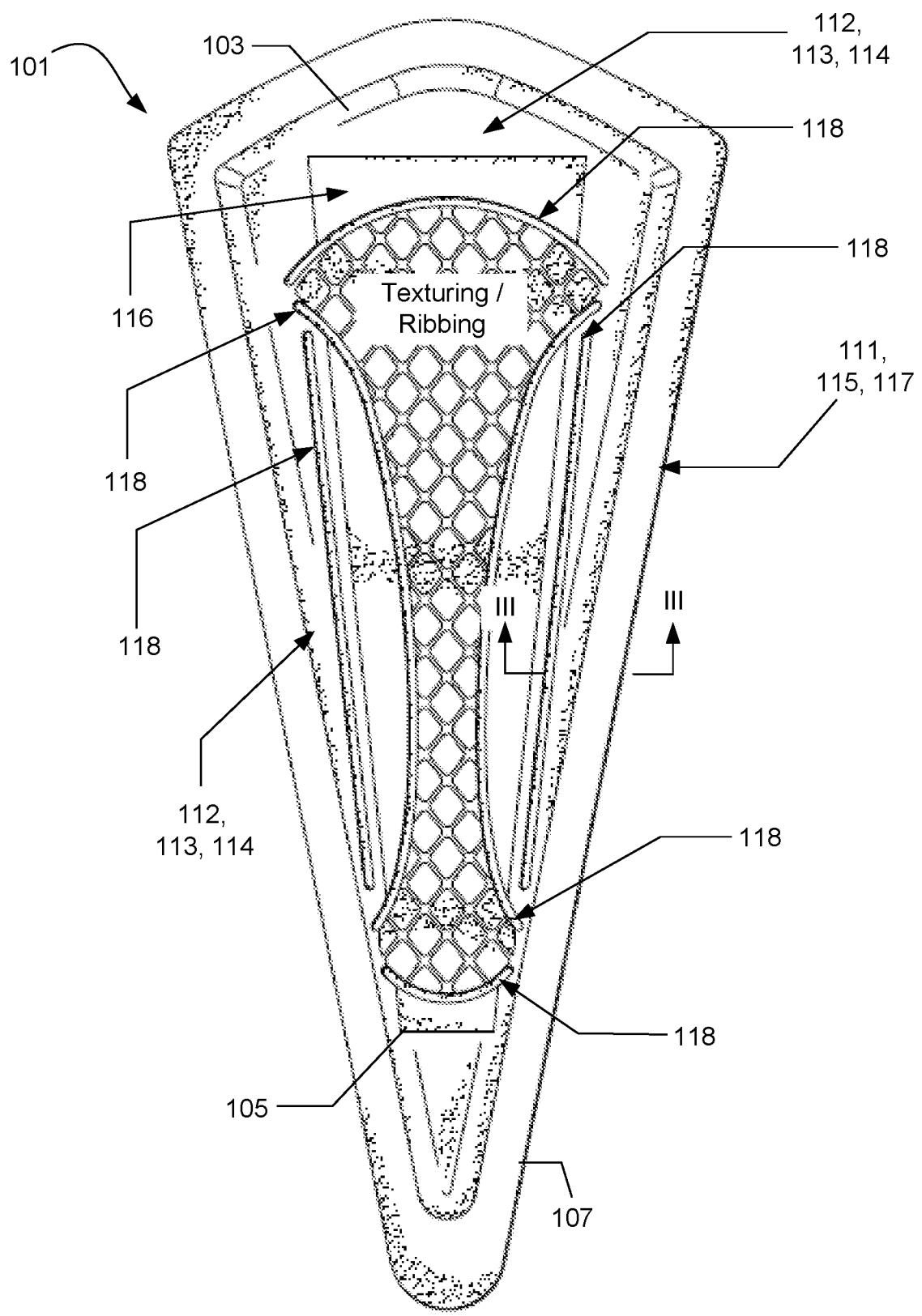
FIG. 2 is a front view of the feminine night pad of FIG. 1.
Figure 3:
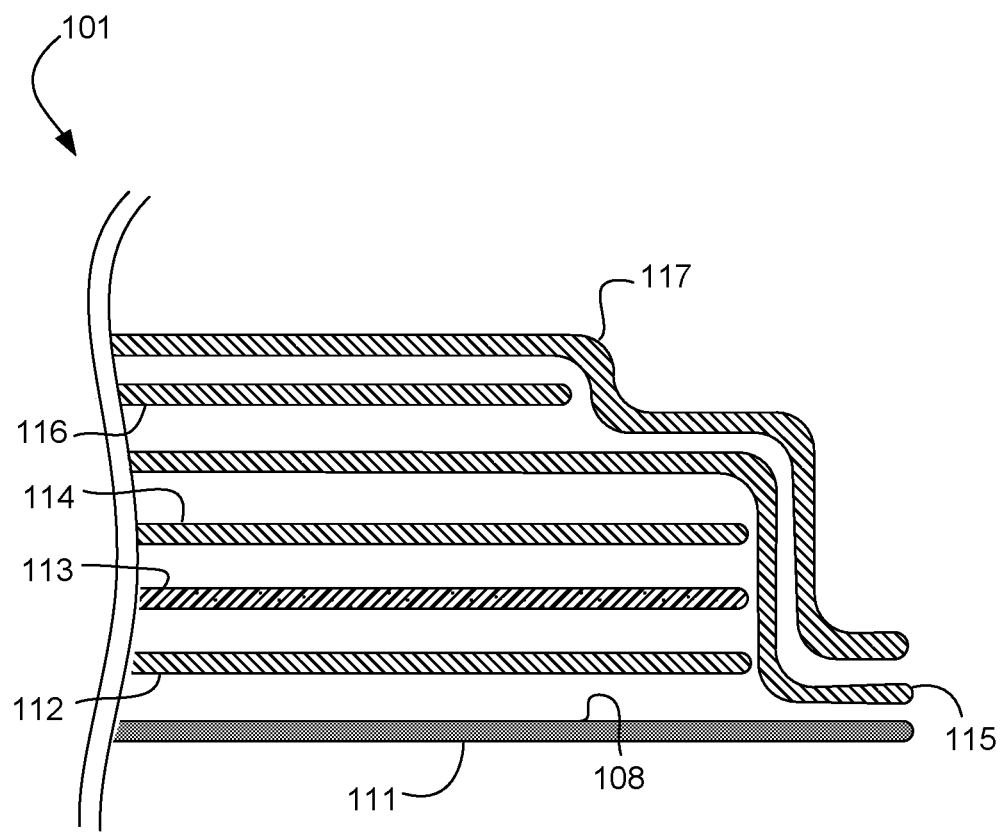
FIG. 3 is a partial section view of the feminine night pad of FIG. 2.
Figure 4:
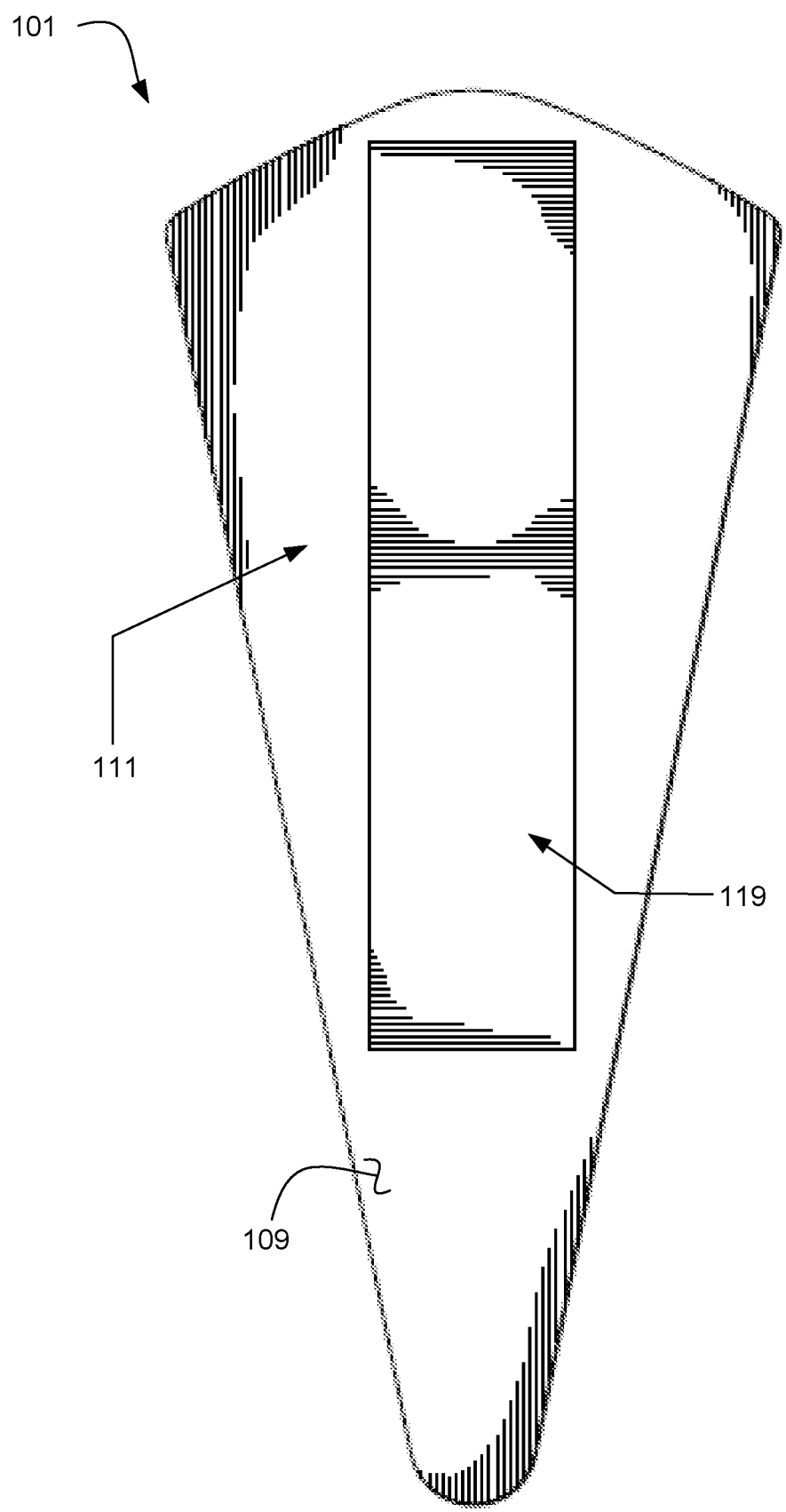
FIG. 4 is a rear view of the feminine night pad of FIG. 2.

1, a perspective view of pad 101 is shown. FIG. 2 illustrates a front view of pad 101. FIG. 3 illustrates an exemplary partial section view wherein the individual layering of pad 101 is shown in greater detail. FIG. 4 provides a rear view of pad 101 for locating an adhesive layer.

Pad 101 includes a multi-level main body having a plurality of absorbing layers. The main body is stepped relative to itself between an initial body portion 103 and a central portion 105. Central portion 105 is thicker and includes more layers than does body portion 103. Central portion 105 is stacked on top of the body portion 103. Central portion 105 includes one or more absorbent strips. Both the body portion 103 and the central portion 105 form the main body of the feminine night pad 101.

Pad 101 further includes a trim member 107 that borders the main body around its entire periphery. Member 107 is thinner and includes fewer layers than does body portion 103. Trim member 107 shares a plurality of absorbing layers with the body portion 103 and the central portion 105 of the body. Each of the layers of pad 101 are stacked or layered along a single surface of trim member 107, such that a top surface 108 is raised as a result of the layering and a rear surface 109 is relatively flat.

The overall shape of pad 101 is that of a triangular form. An upper edge 106 is opposite that of a lower edge 104. Edge 106 is broader than that of edge 104. In fact, the sides of pad 101 are tapered or narrowed in width as it extends away from edge 106, such that edge 104 is almost pointed in shape.

As seen in particular with FIG. 3 in the drawings, the various layering of body portion 103, central portion 105, and trim member 107 are shown. Body portion 103 is formed across plastic sheet 111. Plastic sheet 111 forms a unified bottom layer for the entirety of pad 101. It is typically impermeable. The other layers of pad 101 are in some form or fashion configured to be absorbent and encapsulate liquid.

Central portion 105 is formed of at least three main layers, namely cotton layers 112 and 114 and a gel layer 113. Layer 113 is sandwiched between layers 112 and 114. Body portion 103 is further unified with sheet 111 by the inclusion of layer 115. Layer 115 is a cotton layer that lays across layer 114, wraps over the edge and down the side of the combined layers 112, 113, 114 and then extends over trim member 107. In so doing, all surface area across top surface 108 of member 107 is covered in an absorbent layer (i.e. cotton and gel). A cotton strip layer 116 is laid over layer 115 and is more centrally located on body portion 103. Layer 116 further defines a raised elevation across body portion 103. Layer 116 is further covered by a cotton layer 117 which acts similarly to layer 115 in that it wraps around central portion 105 and body portion 103, and extends over trim member 107. The addition of layers 116 and 117 help to define central portion 105. As stated earlier, all layers apart from trim member 107 are configured to be absorbent. Layer 116 may be made differently from that of the other cotton layers. Examples may include a different weave, thickness, density, or other physical properties.

Across the top surface of layer 117, pad 101 further includes thermo control depressions 118. These depressions are strategically aligned over the surface of layer 117. Depressions 118 are formed by the compressed nature of one or more layers.

For example, depression 118 may be formed by areas where layers 113-117 are compressed together so as to form the depression. Any number of layers may be compressed. Depressions 118 are formed so as to channel the flow of liquid and restrict its ability to reach the sides of pad 101. Depressions 118 may be located on any portion of body portion 103 and central portion 105. Additional texturing and/or ribbing may also be included. This ribbing acts similarly to that of depressions 118 and may also be formed from the compressing of various layers. Any combination of layers may be compressed together (i.e. internal and/or external). One advantage of pad 101 is that the use of cotton layers 115 and 117 extending wholy over sheet 111, the entire surface of pad 101 is adapted for liquid absorption.

As seen in FIG. 4, an adhesive 119 is in communication with rear surface 109. Adhesive 119 is releasably detachable and is configured to secure pad 101 to an undergarment or other piece of clothing. A protective layer may be initially applied across its surface to avoid contamination of adhesive 119.

The current application has many advantages over the prior art including at least the following: (1) a full upper surface covered in absorbent material; (2) unique triangular shape configured to match the shape of a woman's body; (3) use of an absorbent gel; and (4) selective depressions and ribbing across the surface of the pad to minimize liquid travel and increase opportunities of absorption.

The particular embodiments disclosed above are illustrative only and are not intended to be exhaustive or to limit the invention to the precise form disclosed, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A feminine night pad, comprising:
    a body portion having a plurality of absorbing layers, the absorbing layers of the body portion include a gel layer and a plurality of cotton layers with the gel layer located between the plurality of cotton layers;
    a central portion within a perimeter of the body portion, the central portion including one or more absorbent strips stacked on top of the body portion, the body portion and the central portion forming a main body of the feminine night pad; and
    a trim member extending around the periphery of the main body, the trim member having a plurality of cotton absorbing layers that also extend over the body portion and the central portion of the main body, the cotton absorbing layers of the trim member being included into the body portion and the central portion;
    wherein at least one of the one or more absorbent strips separate the plurality of cotton absorbing layers of the trim member within the central portion; and
    wherein the trim member and the main body is formed into a triangular shape.

2. The pad of claim 1, further comprising:
    an adhesive on a rear surface of the trim member.

3. The pad of claim 1, wherein the trim member includes a plastic sheet that spans under the main body, the plastic sheet defining a rear surface.

4. The pad of claim 1, wherein the one or more absorbent strips are shaped similarly to that of the main body.

5. The pad of claim 1, wherein the main body includes a ribbed area configured to confine and slow the flow of fluid.

6. The pad of claim 1, further comprising:
a depression configured to channel the flow of liquid.

7. The pad of claim 6, wherein the depression is located partially in the central portion.

8. The pad of claim 6, wherein the depression is located partially in the body portion.

* * * * *